(12) United States Patent
Shiber

(10) Patent No.: US 6,758,851 B2
(45) Date of Patent: *Jul. 6, 2004

(54) VESSEL CLEANER

(76) Inventor: Samuel Shiber, 365 Kearney Cir., Manchester, NH (US) 03104

( * ) Notice: Subject to any disclaimer, the term of this patent is extended or adjusted under 35 U.S.C. 154(b) by 505 days.

This patent is subject to a terminal disclaimer.

(21) Appl. No.: 09/867,307

(22) Filed: May 29, 2001

(65) Prior Publication Data
US 2002/0165567 A1 Nov. 7, 2002

Related U.S. Application Data

(63) Continuation-in-part of application No. 09/654,934, filed on Sep. 1, 2000, which is a continuation-in-part of application No. 09/389,712, filed on Sep. 3, 1999, now Pat. No. 6,143,009, which is a continuation-in-part of application No. 09/241,802, filed on Feb. 2, 1999, now abandoned.

(60) Provisional application No. 60/118,611, filed on Feb. 4, 1999.

(51) Int. Cl.⁷ .............................................. A61B 17/32
(52) U.S. Cl. ....................................................... 606/159
(58) Field of Search ................................ 606/159, 170, 606/167, 180; 604/22

(56) References Cited

U.S. PATENT DOCUMENTS

| 4,030,503 A | * | 6/1977 | Clark, III ................... 606/159 |
| 4,228,802 A | | 10/1980 | Trott |
| 4,857,046 A | | 8/1989 | Stevens et al. |
| 4,986,807 A | | 1/1991 | Farr |
| 4,994,067 A | | 2/1991 | Summers |
| 5,002,553 A | | 3/1991 | Shiber |
| 5,007,896 A | | 4/1991 | Shiber |
| 5,009,659 A | | 4/1991 | Hamlin et al. |
| 5,011,490 A | | 4/1991 | Fischell et al. |
| 5,024,651 A | | 6/1991 | Shiber |
| 5,026,384 A | | 6/1991 | Farr et al. |
| 5,059,203 A | | 10/1991 | Husted |
| 5,074,841 A | | 12/1991 | Ademovic et al. |
| 5,087,265 A | | 2/1992 | Summers |
| 5,097,849 A | | 3/1992 | Kensey et al. |
| 5,100,426 A | | 3/1992 | Nixon |
| 5,102,415 A | | 4/1992 | Guenther |
| 5,116,350 A | | 5/1992 | Stevens |
| 5,135,531 A | | 8/1992 | Shiber |
| 5,154,724 A | | 10/1992 | Andrews |
| 5,158,564 A | | 10/1992 | Schnepp-Pesch et al. |
| 5,192,268 A | | 3/1993 | Shiber |
| 5,192,291 A | | 3/1993 | Pannek |
| 5,195,954 A | * | 3/1993 | Schnepp-Pesch et al. ..... 604/22 |
| 5,201,750 A | | 4/1993 | Hocherl et al. |
| 5,205,822 A | | 4/1993 | Johnson |
| 5,217,474 A | | 6/1993 | Zacca et al. |
| 5,232,445 A | | 8/1993 | Bonzel |
| 5,234,451 A | | 8/1993 | Osypka |
| 5,242,460 A | | 9/1993 | Klein et al. |
| 5,242,461 A | | 9/1993 | Kortenbach et al. |
| 5,248,296 A | | 9/1993 | Alliger |
| 5,250,059 A | | 10/1993 | Andreas et al. |
| 5,261,877 A | | 11/1993 | Fine et al. |
| 5,269,751 A | | 12/1993 | Kaliman et al. |

(List continued on next page.)

Primary Examiner—Kathryn Odland
(74) Attorney, Agent, or Firm—Samuel Shiber

(57) ABSTRACT

An apparatus for extracting an obstruction located in a patient's vessel by fragmenting the obstruction and conveying the fragments through the apparatus out of the patient's body, having a flexible-tube with an open distal end, connected to a negative pressures, a motor-rotated, flexible, spiral conveyor-shaft disposed in the flexible tube that conveys the obstruction fragments, cooperatively with the negative pressure, through the flexible tube and an offset agitator that is connected to and is rotated by the flexible conveyor-shaft to fragment the obstruction. The offset-agitator can be moved in and out of the flexible tube, through the open distal end, to adjust its effective diameter.

44 Claims, 3 Drawing Sheets

U.S. PATENT DOCUMENTS

| | | |
|---|---|---|
| 5,282,484 A | 2/1994 | Reger |
| 5,284,486 A | 2/1994 | Kotula et al. |
| 5,290,232 A | 3/1994 | Johnson |
| 5,306,244 A | 4/1994 | Shiber |
| 5,312,425 A | 5/1994 | Evans et al. |
| 5,312,427 A | 5/1994 | Shturman |
| 5,314,438 A | 5/1994 | Shturman |
| 5,334,211 A | 8/1994 | Shiber |
| 5,336,167 A | 8/1994 | Sullivan et al. |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,358,509 A | 10/1994 | Fine et al. |
| 5,366,464 A | 11/1994 | Belknap |
| 5,368,603 A | 11/1994 | Halliburton |
| 5,370,609 A | 12/1994 | Drasler et al. |
| 5,370,651 A | 12/1994 | Summers |
| 5,370,653 A | 12/1994 | Cragg |
| 5,376,100 A | 12/1994 | Lefebvre |
| 5,395,311 A | 3/1995 | Andrews |
| 5,402,790 A | 4/1995 | Jang et al. |
| 5,403,334 A | 4/1995 | Evans et al. |
| 5,417,703 A | 5/1995 | Brown et al. |
| 5,419,774 A | 5/1995 | Willard et al. |
| 5,423,799 A | 6/1995 | Shiu |
| 5,441,510 A | 8/1995 | Simpson et al. |
| 5,449,369 A | 9/1995 | Imran |
| 5,490,859 A | 2/1996 | Mische et al. |
| 5,501,694 A | 3/1996 | Ressemann et al. |
| 5,507,292 A | 4/1996 | Jang et al. |
| 5,507,760 A | 4/1996 | Wynne et al. |
| 5,507,761 A | 4/1996 | Duer |
| 5,512,044 A | 4/1996 | Duer |
| 5,514,151 A | 5/1996 | Fogarty et al. |
| 5,522,824 A | 6/1996 | Ashby |
| 5,522,825 A | 6/1996 | Kropf et al. |
| 5,522,826 A | 6/1996 | Daily |
| 5,527,326 A | 6/1996 | Hermann et al. |
| 5,540,707 A | 7/1996 | Ressemann et al. |
| 5,554,114 A | 9/1996 | Wallace |
| 5,554,163 A | 9/1996 | Shturman |
| 5,556,405 A | 9/1996 | Lary |
| 5,556,408 A | 9/1996 | Farhat |
| 5,569,275 A | 10/1996 | Kotula et al. |
| 5,569,277 A | 10/1996 | Evans et al. |
| 5,571,130 A | 11/1996 | Simpson et al. |
| 5,584,843 A | 12/1996 | Wulfman et al. |
| 5,626,593 A | 5/1997 | Imran |
| 5,630,823 A | 5/1997 | Schmitz-Rode et al. |
| 5,632,755 A | 5/1997 | Nordgren et al. |
| 5,643,296 A | 7/1997 | Hundertmark et al. |
| 5,643,297 A | 7/1997 | Nordgren et al. |
| 5,643,298 A | 7/1997 | Nordgren et al. |
| 5,649,941 A | 7/1997 | Lary |
| 5,653,722 A | 8/1997 | Kieturakis |
| 5,658,301 A | 8/1997 | Lemaitre et al. |
| 5,658,302 A | 8/1997 | Wicherski et al. |
| 5,662,603 A | 9/1997 | Gelbfish |
| 5,669,920 A | 9/1997 | Conley et al. |
| 5,674,232 A | 10/1997 | Halliburton |
| 5,681,336 A | 10/1997 | Clement et al. |
| 5,688,234 A | 11/1997 | Frisbie |
| 5,690,642 A | 11/1997 | Osborne |
| 5,695,506 A | 12/1997 | Pike et al. |
| 5,695,507 A | 12/1997 | Auth |
| 5,695,508 A | 12/1997 | Chigogidze |
| 5,702,413 A | 12/1997 | Lafontaine |
| 5,755,775 A | 5/1998 | Trerotola |
| 5,766,191 A | 6/1998 | Trerotola |
| 5,772,674 A | 6/1998 | Nakhjavan |
| 5,779,721 A | 7/1998 | Nash |
| 5,785,675 A | 7/1998 | Drasler |
| 5,792,157 A | 8/1998 | Mische |
| 5,827,229 A | 10/1998 | Auth |
| 5,836,868 A | 11/1998 | Ressemann |
| 5,843,022 A | 12/1998 | Willard |
| 5,843,103 A | 12/1998 | Wulfman |
| 5,873,882 A | 2/1999 | Straub |
| 5,876,414 A | 3/1999 | Straub |
| 5,879,361 A | 3/1999 | Nash |
| 6,036,708 A * | 3/2000 | Sciver ............. 606/159 |
| 6,090,118 A | 7/2000 | McGuckin, Jr. |
| 6,143,009 A * | 11/2000 | Shiber ............ 606/159 |
| 6,156,046 A * | 12/2000 | Passafaro et al. ........ 606/159 |
| 6,206,898 B1 | 3/2001 | Honeycutt et al. |
| 6,217,595 B1 * | 4/2001 | Shturman et al. ......... 606/159 |
| 6,235,042 B1 | 5/2001 | Katzman |
| 6,322,572 B1 * | 11/2001 | Lee ............... 606/159 |
| 6,440,148 B1 * | 8/2002 | Shiber ............ 606/159 |
| 6,454,775 B1 * | 9/2002 | Demarais et al. ........ 606/128 |
| 6,482,215 B1 * | 11/2002 | Shiber ............ 606/159 |
| 6,602,264 B1 * | 8/2003 | McGuckin, Jr. ......... 606/159 |
| 6,620,172 B1 * | 9/2003 | Dretler et al. .......... 606/128 |
| 2003/0028206 A1 * | 2/2003 | Shiber ............ 606/159 |
| 2003/0187468 A1 * | 10/2003 | Shiber ............ 606/159 |
| 2003/0191483 A1 * | 10/2003 | Cooke et al. ......... 606/159 |
| 2003/0216761 A1 * | 11/2003 | Shiber ............ 606/159 |

* cited by examiner

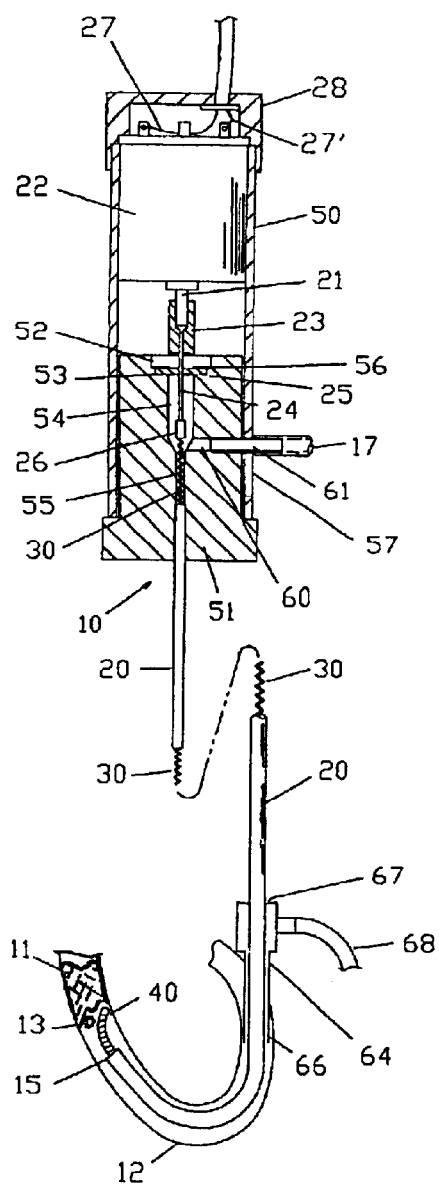
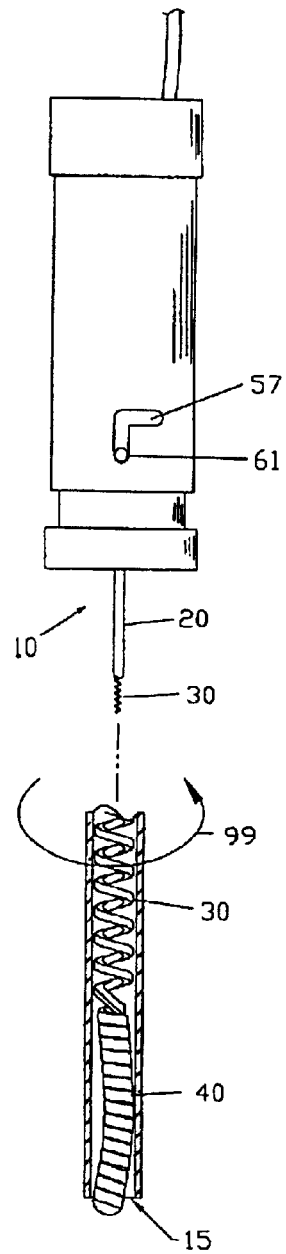
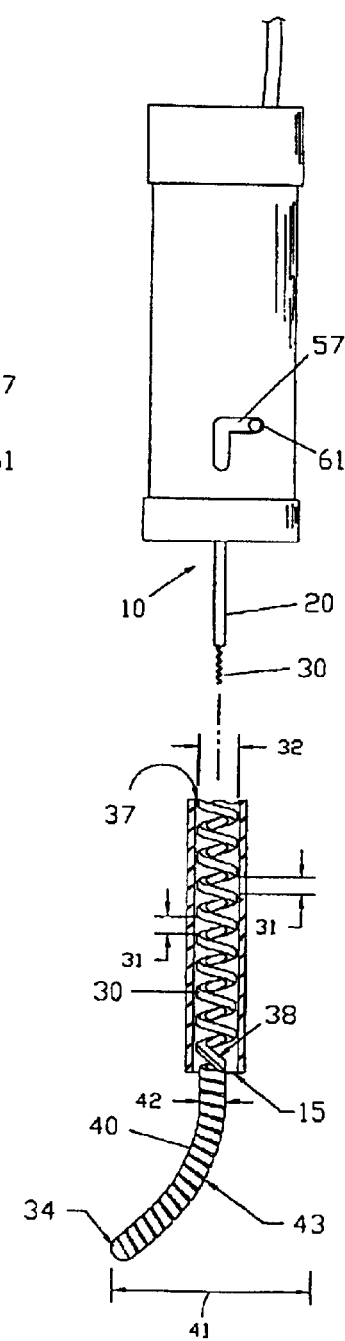
FIG. 1
FIG. 3
FIG. 2

VESSEL CLEANER

CROSS REFERENCE TO OTHER APPLICATIONS

This application is a continuation in part (CIP) of my co-pending application Ser. No. 09/654,934 filed on Sep. 1, 2000 that is a CIP of my earlier application Ser. No. 09/389,712 filed on Sep. 3, 1999 (now U.S. Pat. No. 6,143,009) that is a CIP of Ser. No. 09/241,802 filed on Feb. 2, 1999 (abandoned). This application also relies for priority on my application PCT/US00/01797 filed on Jan. 25, 2000 that relies for priority on the above mentioned Ser. No. 09/389,712 and Ser. No. 09/241,802 and on a provisional application S. No. 60/118,611 filed on Feb. 4, 1999. All the above prior applications are being incorporated herein by reference.

BACKGROUND AND SUMMARY OF THE INVENTION

Current pharmacological, surgical or trans-catheter procedures for opening clogged vessels can be time-consuming, traumatic and expensive.

Objects of the present invention are to provide a flexible apparatus that can be inserted into a patient's vessel, for example a blood vessel, through a small puncture wound, be navigated to an obstruction, for example thrombus, fragment the obstruction to small pieces, aspirate pieces of the obstruction into the apparatus and simultaneously convey the pieces by a combination of negative pressure and mechanical conveyance. These and other objects of the invention will become apparent from the following discussion and the accompanying drawings.

BRIEF DESCRIPTION OF THE FIGURES

In the following FIGS. the midsection of the embodiments is represented by a short phantom line to enable to fit the FIGS. on the drawing sheet and the embodiments' distal section is enlarged to show certain details.

FIG. 1 shows an apparatus according to the present invention, with its distal end inserted into a curved vessel.

FIG. 2 shows the apparatus with the distal end section further enlarged.

FIG. 3 shows the apparatus with its offset agitator pulled in.

DETAILED DESCRIPTION OF THE FIGURES

Figures 4, 5, 6, 7, 8:
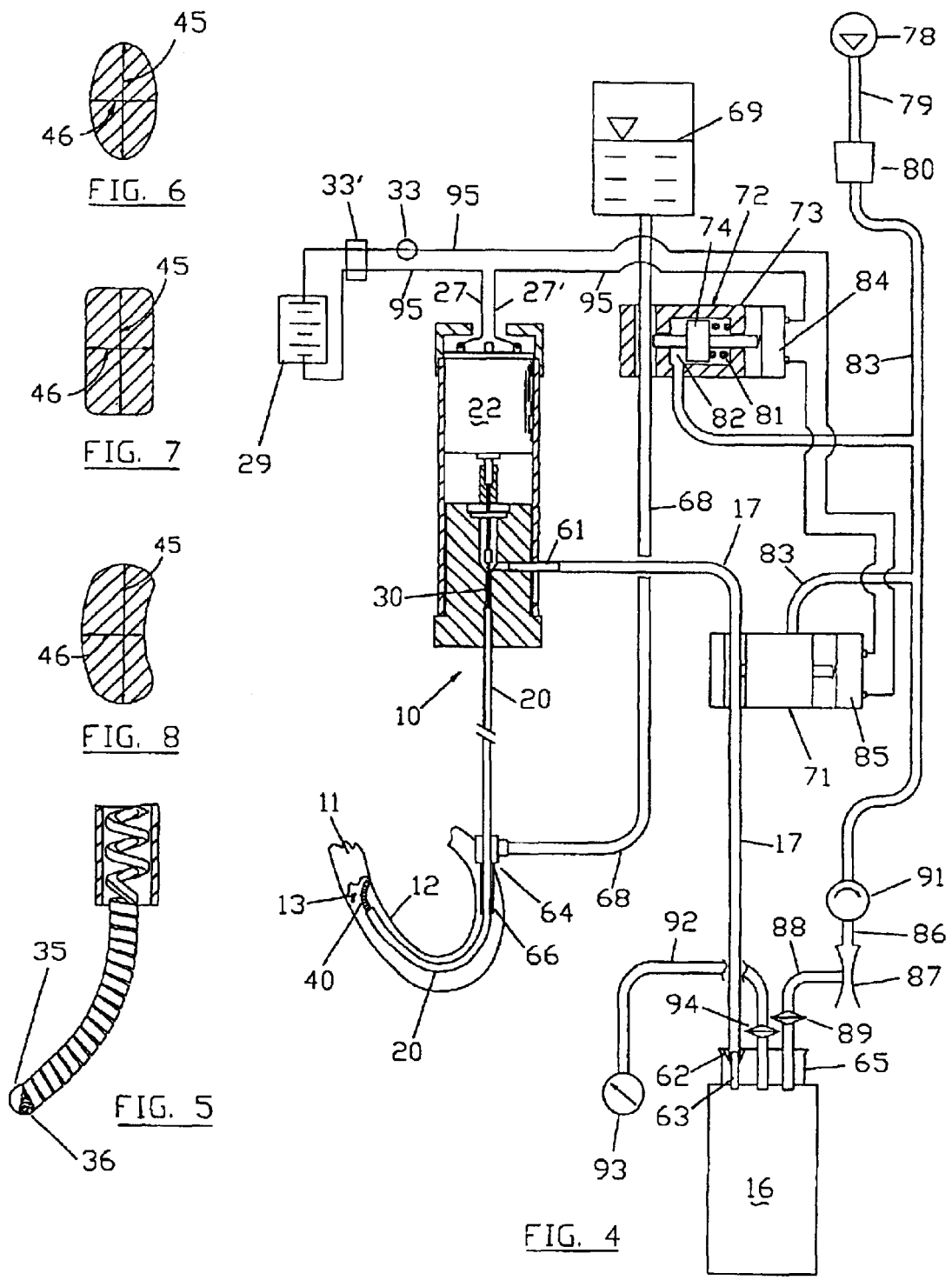
FIG. 4 schematically shows controls of the apparatus.
FIG. 5 shows the distal end section of an offset agitator with a modified tip.
FIGS. 6, 7 and 8 show cross sections of flattened wires.

FIG. 1 shows an apparatus 10 for extracting an obstruction 11 (e.g., thrombus) located in a patient's vessel 12 (e.g., graft, vein, artery) by fragmenting the obstruction and conveying fragments 13 of the obstruction through the apparatus and out of the patient's body. The apparatus comprises a flexible-tube 20 containing a motor-rotateable conveyor-shaft 30 to which an offset-agitator 40 is connected.

The flexible-tube 20 (similar parts shall be denoted by the same numerals throughout the FIGS.) has an open distal end 15 ("distal end" referring to the end that goes further into the vessel and "proximal end" referring to the other end) and is connected to a collection bottle 16 (note also FIG. 4) by a line 17. Negative pressure in the collection bottle (negative pressure as used in this application means a pressure lower than the pressure in the vessel) urges the fragments to move through the open distal end 15 into the flexible tube 20 and through the flexible-tube 20 into the collection bottle 16.

The conveyor-shaft 30, disposed in the flexible-tube 20, is rotatable by an output shaft 21 of an electrical motor 22 through a coupling 23 that is preferably made of an electrically non-conductive material and is also connected to a shaft 24. The shaft 24 is connected, e.g., by a weld, to the proximal end of the conveyor-shaft 30 with a short sleeve 26 that reinforces the welded section of the conveyor-shaft 30. The diameter of the shaft 24 is preferably small to reduce the frictional losses and leakage between the shaft 24 and a seal 25.

As illustrated in FIG. 4, the motor 22 is driven by an electrical current supplied to it by a battery 29 through circuit 95 and wires 27 and 27'(alternative motors can be used, e.g., air powered motors). At least a part of the conveyor-shaft 30, and preferably substantially all of its length, is a spiral with gaps 31 (note also FIGS. 2 and 10) between its coils to enable the spiral to convey the fragments 13. The gap between the spiral's coils could be varied over the length of the conveyor-shaft to affect and control the operation of the apparatus. For example, in coronary versions of the apparatus that tend to be long (e.g., three to five feet) the gaps between the coils of the proximal section may be increased since the proximal section is commonly disposed in the patient's less curved aorta and does not have to be very flexible. At the same time the increased stiffness reduces the longitudinal expansion of the proximal section of the conveyor-shaft and reduces unintentional changes in the position of the offset agitator relative to the open distal end of the flexible tube.

The direction of rotation of the conveyor-shaft's spiral is such (the direction of rotation is illustrated by an arrow 99 on FIG. 3) that as it rotates relative to the flexible-tube 20 it conveys the fragments, cooperatively with the negative pressure, from the open distal end 15 through the flexible-tube 20. The relative rotation between the conveyor-shaft 30 and the flexible-tube 20 also reduces the friction that would tend to inhibit the conveyance of the obstruction fragments through the flexible-tube 20.

The offset-agitator 40 extends at least partially out of the open distal end 15 of the flexible-tube 20 and is connected to and rotated by the distal end of the conveyor-shaft 30 to fragment the obstruction 11 while rotating with an effective diameter 41 (note also FIG. 2) that is larger than the outer diameter 42 of the conveyor-shaft 30. The offset-agitator 40 and the spiral that forms the conveyor-shaft 30 are preferably made from one continuous piece of wire. Thus the conveyor-shaft 30 and the offset-agitator 40 are connected one to the other with a high degree of integrity and with minimal structural bulk, bulk that would have interfered with the entry of fragments into the flexible-tube 20. Gaps between the coils 43 of the offset-agitator 40 are substantially smaller than the gaps 31 between the coils of the conveyor-shaft to minimize the likelihood of the offset-agitator 40 becoming entangled with protrusions that occasionally hang from and are attached to the vessel's walls, whereas the conveyor-shaft 30 is shielded from such protrusions since it is covered by the flexible tube 20, and it is designed to engage and convey fragments 13 that were broken off from the obstruction 11.

To further minimize the likelihood that the offset-agitator 40 tangles or damages vessel walls the tip of the distal agitator 34 can be rounded. A preferred method of rounding the tip, that yields a high degree of structural integrity, is melting the distal end of the wire that forms the offset agitator to reform to a smooth rounded sphere 34. In the event that the offset-agitator 40 does become entangled or that the apparatus becomes clogged it is often possible to rectify the problem by briefly reversing the direction of rotation of the motor by reversing the current direction in circuit 95 with switch 33'.

A modified tip of the offset agitator is shown in FIG. 5. Since the geometry of the offset-agitator 40 makes a portion of its tip 36 more likely to contact the obstruction and less likely to contact the vessel's wall, this portion can be made rougher to more effectively fragment the obstruction material and a portion 35 of the tip that faces the vessel's wall is preferably made smoother.

Figure 10:
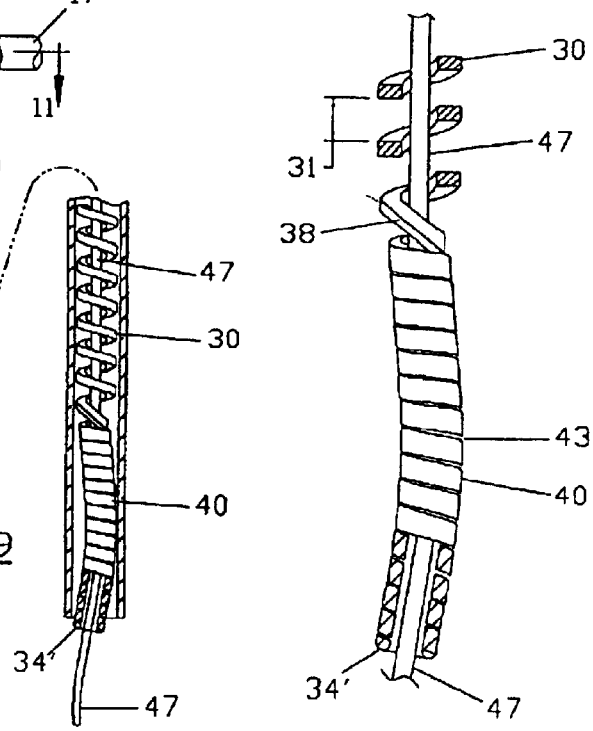
FIG. 10 shows a further enlargement of the offset agitator shown in FIG. 9.

Referring to FIGS. 2 and 10, the conveyor-shaft 30 and the offset-agitator 40 are preferably made from one piece of a continuous flattened spiral wire where the conveyor-shaft 30 is wound on its edge and the offset-agitator 40 is wound on its side, and the two are connected by a short twisted section 38 where the wire transitions from being wound on its edge to being wound on its side. The connection 38 being an integral part of the spiral wire has a high degree of integrity and it is streamlined so that it does not block fragments from entering the gaps 31 between the coils of the conveyor shaft.

FIGS. 6, 7, and 8 illustrate examples of flattened-wires (the term "flattened-wire", as used in this application, is derived from a preferred method of manufacturing such wire by flattening a wire with a round cross section between two adjacent rollers). The flattened-wires have a non-round cross section with a long-axis 45 and a short-axis 46 and, as used in this application, the term edge refers to a narrower side of the cross section and the term side refers to the wider side of the cross section. Thus, the term "wound on its edge" refers to the wire wound with its short-axis being approximately parallel to the spiral's longitudinal axis as the conveyor shaft is illustrated throughout the FIGS. The term "wound on its side" refers to the wire wound with its long-axis being approximately parallel to the spiral's longitudinal axis as the offset agitator is illustrated throughout the FIGS.

A conveyor-shaft made of a flattened-wire, as compared to a conveyor-shaft made of a wire having a round cross section with the same number of coils and the same torque carrying capacity, has increased gaps 31 between the coils for conveying the fragments and also has increased flexibility which in turn reduces the side force that the apparatus imparts on a curved vessel's wall. Additionally, when a piece of flattened wire is wound on a mandrel, to form both the conveyor-shaft and offset agitator, the outer diameter of the conveyor-shaft 32 is larger than the outer diameter of the distal-agitator 42 and the annular ring defined between a diameter 32 and a diameter 42 increases the area through which fragments can enter the flexible tube 20. For example when a flattened wire having a long-axis measuring 0.016 inch and a short-axis measuring 0.008 inch is wound into a spiral with an internal diameter of 0.020 inch it yields a conveyor-shaft with an outer diameter of 0.052 inch and an offset agitator with an outer diameter of 0.036 inch.

A diametrical clearance 37 between the conveyor-shaft 30 and the flexible tube 20 (as measured when the apparatus is not curved) allows the conveyor-shaft to freely rotate in the flexible tube. However, as the apparatus 10 is inserted into a curved vessel (note FIG. 1) this clearance decreases. Thus, the diametrical clearance 37 (as measured when the apparatus is not curved) has to be large enough so that the conveyor-shaft remains free to rotate even when the apparatus is operated in a curved vessel. For example, in an apparatus having a conveyor-shaft 30 with an outside diameter of 0.052 inch a minimal clearance of about 0.004 inch is required for the apparatus to operate in a vessel with a radius of curvature of one inch.

To decrease the size of the puncture wound that is needed to insert the apparatus into the vessel and to decrease the side force that the apparatus exerts on the vessel's wall, a thin-walled non-reinforced flexible-tube 20 is preferable. However, a thin-walled non-reinforced tube tends to kink when it is forced to assume a tightly curved configuration. To counter this tendency a reinforcement (e.g., a spiral steel wire) can be integrated into the tube's wall. However, such a solution would increase the wall's thickness and as a result the diameter of the puncture wound would increase by twice the increase in wall thickness. Further, such reinforcement stiffens the flexible-tube 20 and increases the side force that the apparatus exerts on the vessel's wall, thus increasing the impact that the rotating offset-agitator 40 imparts on the curved section of the vessel. Therefore, the present invention relies on the conveyor-shaft 30 to prevent the flexible-tube 20 from bending too sharply and to the extent that kinking starts to develop, if the clearance is sufficiently small, the conveyor-shaft is able to radially support the flexible-tube 20 and prevent it from kinking further. For example, in an apparatus having a conveyor-shaft 30 with an outside diameter of 0.052 inch a clearance of than 0.010 inch enables the conveyor-shaft to radially support and prevent kinking in the flexible-tube in a curve with a radius of 1 inch.

Using a non-reinforced flexible-tube and making it from a transparent material allows light transmission across the wall of the flexible-tube 20 thus permitting visual inspection of the conveyance process, and it further allows to transmit light along the wall using the flexible-tube as a light guide to transmit light into and out of the vessel.

Referring back to FIG. 1, the motor 22 is housed in and affixed to one end of a cylinder 50 which is closed by a cover 28. The other end of the cylinder 50 contains a hub 51 which can slide out of the cylinder a limited amount. The hub defines a hole through its center that has stepped diameters 52, 53, 54 and 55. The seal 25 is seated in diameter 53 and is held in place by a retaining ring 56 seated in diameter 52. The flexible-tube 20 is bonded to the hub 51 inside diameter 55. An evacuation port 60 intersects with and connects to the stepped hole. A short rigid tube 61 passes through an "L"-shaped slot 57, defined in the cylinder 50, and is affixed in the port 60. One leg of the "L"-shaped slot permits a limited telescoping movement of the hub 51 (e.g., movement of about a quarter of an inch), together with the flexible-tube 20, relative to the cylinder 50 which in turn causes the open distal end 15 to move relative to the offset-agitator 40 since the offset-agitator 40 is connected through the conveyor-shaft 30 to the motor and thereby to the cylinder 50. This telescoping movement (as the apparatus is adjusted from the position shown in FIG. 2. to the poistion shown in FIG. 3) causes the effective diameter of the distal-agitator to decrease and it can be used to assist in inserting the apparatus through an introducer-sheath 64, equipped with a seal 67, into the vessel (with the distal-agitator preferably pulled into the flexible tube as shown in FIG. 3) and in navigating the apparatus through obstructed areas and bifurcations in the vessel and through other such areas that require steering the distal end of the apparatus.

The negative pressure line 17 connects the rigid tube 61 to a second rigid tube 63 (note FIG. 4) that fits in a conical seat 62 formed in a cap 65 of the collection bottle 16. An infusion line 68 connects an inlet port of the introducer sheath 64 to a source of a pressurized mixture of preferably saline, radio-opaque fluid and some heparin 69 that the introducer-sheath delivers to the vessel through its sheath 66. Lines 17 and 68 pass through the valves 71 and 72, respectively. The valves 71 and 72 pinch and thereby shut off the flow through the lines when the motor 22 is selectably disabled.

Figure 9:
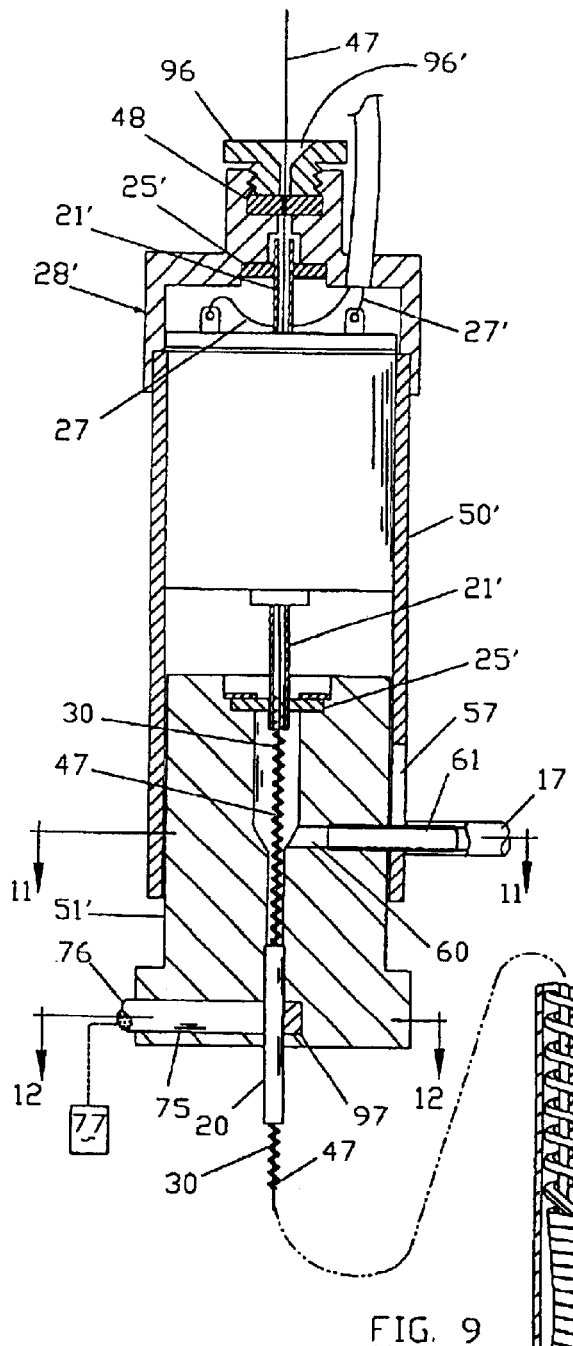
FIG. 9 shows a modified apparatus, deliverable over a guidewire.
Figure 11:
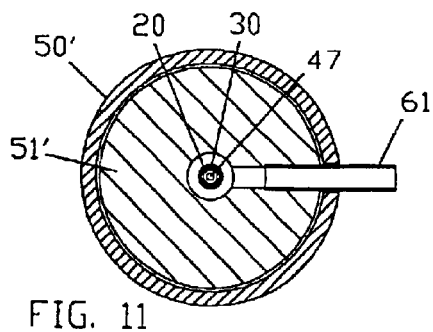
FIG. 11 shows a cross section of FIG. 9 along line 11—11.
Figure 12:
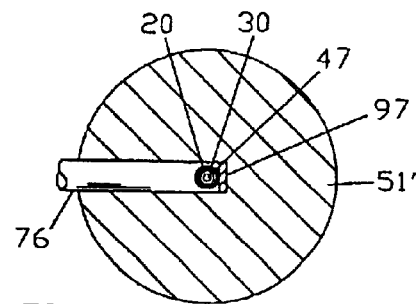
FIG. 12 shows a cross section of FIG. 9 along line 12—12.

As explained above, the flexible-tube 20 is preferably transparent to allow observation of the movement of the fragments through the flexible-tube 20. Additionally, it can be used as a light guide to transmit light into or out of the vessel. FIG. 9 shows a modified hub 51' that defines a hole 75 which accepts a first end of a flexible fiber optic light guide 76 that is optically coupled (so that it transmits light) to the flexible-tube 20 and a mirror 97 that reflects escaping light back into the flexible-tube 20. A second end of the light guide 76 is optically coupled to a continuous or intermittent (stroboscopic) light source 77 (alternatively numeral 77 can indicate an imaging device). Such lighting can be used to illuminate inside of the vessel and, where the vessel is sufficiently close to the patient's skin, to provide external indication of the location of the device.

FIG. 9 also shows an apparatus that has been modified to be delivered to an is obstruction site over a guidewire 47. The modifications comprise making the tip 34' hollow, making a motor shaft 21' a tube section and extending it into a modified cover 28'. The cover 28' supports a motor-seal 25' that seals around the motor shaft and a seal 48 that seals around the guidewire and is packed in place by a threaded insert 96 that defines a cone 96' to ease insertion of the guidewire 47. These modifications establish a continuous uninterrupted passage through the apparatus that starts at the modified tip 34', continues through the offset-agitator 40, through the conveyor-shaft 30, through the modified motor shaft 21' and the modified cover 28'.

The effective diameter of the distal-agitator can be adjusted by pulling or pushing it into or out of the distal opening of the flexible-tube 20 as illustrated in FIGS. 2 and 3 and optionally the distal-agitator can be rotated to assist in the process of navigating it. However, when a modified system is advanced over a guidewire, it is preferable to pull the offset-agitator 40 into the flexible-tube 20, as shown in FIG. 9, to thereby reduce the curvature of the continuous passage to ease sliding the apparatus over the guidewire except that the offset agitator can be extended out of the open distal end 15 over the guidewire to slightly bend the guidewire to enhance the steering capability of the apparatus.

As illustrated in FIG. 4 the introducer-sheath 64 is connected to a pressurized mixture of saline and radio-opaque fluid 69 through an infusion line 68, and the flexible-tube 20 is connected to negative pressure through a line 17 and the lines pass through pinch valves 72 and 71, respectively, that shut off the flow through the lines when the motor is shut off.

FIG. 4 further illustrates the controls of the apparatus. The valve 72 has a housing 73 in which a piston 74 is slideable. Normally, the piston is urged by a spring 81 to pinch and thereby shut off the line 68. However, when pressure is supplied to an air tight cavity 82 through line 83 the piston moves against the spring 81 and closes a switch 84. Valve 71, which is constructed and operates similarly to valve 72, shuts off line 17 and closes switch 85 at the same time A pressurized air (or another pressurized gas, e.g. nitrogen) source 78 is connected to a master valve 80 through a line 79. The master valve 80 is connected by lines 83 to the pinch valves 71, 72 and to a manually adjustable pressure regulator 91. The pressure regulator 91 supplies regulated pressure to a Venturi-type pump 87 through a line 86. The pump 87 increases the negative pressure in the collection bottle 16 through a line 88. The level of the negative pressure that the pump 87 generates corresponds to the level of the air pressure it receives from the pressure regulator 91. A vacuum gauge 93 is connected to the collection bottle by a line 92 and displays pressure prevailing in the collection bottle 16.

Lines 92 and 88 contain microbial barriers 94 and 89, respectively, that can be used to separate preferably disposable parts such as the apparatus 10 and collection bottle 16, and keep uncontaminated the reusable parts such as the valves and gauge.

The motor 22 is connected in series, by an electrical circuit 95, to a battery 29, switches 84, 85 and a power regulator switch 33 by which the electrical power supplied to the motor can be manually adjusted. A double pole double throw switch 33' can be used to momentarily reverse the direction of the current in the circuit 95 and thereby momentarily reverse the direction of rotation of the shaft 21.

Operation

A process for extracting an obstruction from within a patient's vessel and out of the patient's body using an apparatus according to the present invention comprises:

Gaining access to the obstructed vessel, or to another vessel leading to the obstructed vessel by inserting an introducer-sheath 64 into the vessel and inserting the apparatus 10, through the introducer-sheath into the vessel 12.

Advancing the apparatus towards the obstruction while steering it past bifurcations and obstacles, adjusting the effective diameter of the offset-agitator and/or rotating the offset-agitator along the way if needed.

Activating the system by opening the master valve 80 that supplies pressurized air to the pump 87 (which in turn increases the negative pressure in the bottle 16) and to the pinch valves 71 and 72. Pinch valve 71 opens the line 17 and thereby connects the apparatus to negative pressure. Pinch valve 72 opens the infusion line 68 and thereby supplies, through the introducer-sheath 64, a pressurized mixture of saline, radio-opaque fluid and some heparin to the vessel. When a long apparatus is used, for example to treat coronary vessels, a guiding-catheter (of the type that is commonly used to guide and deliver interventional devices to the coronary arteries) can be inserted into the introducer sheath to guide the apparatus and introduce it into the coronary vessels. Where a guiding catheter is used, the infusion line 68 is preferably connected to the guiding catheter to deliver through it the mixture of saline, radio opaque fluid and heparin further into the vessel and closer to the obstruction site than can be done with a standard introducer sheath. Thus, the term introducer, as used in this application, denotes an introducer sheath and/or guiding catheter that provide access for the apparatus and for infusion of fluids into the vessel.

At the same time that pinch valves 71 and 72 open the lines 17 and 68 they close the switches 85 and 84 and thereby complete the electrical circuit 95 delivering electrical power to the motor 22 through wires 27 and 27', causing the motor's output shaft 21 to rotate the flexible conveyor-shaft 30 in the flexible-tube 20 which in turn causes the rotation of the offset-agitator 40 in the vessel 12.

As the apparatus is moved longitudinally in the vessel the offset agitator 40 fragments the obstruction 11 and the negative pressure draws fragments of the obstruction into the flexible-tube 20 where the negative pressure cooperatively with the mechanical action of the conveyor-shaft 30 moves the fragments from the open distal end 15 through the flexible-tube 20.

While the present invention has been illustrated by a limited number of embodiments, it should be understood that modifications and substitutions may be made within the spirit of the invention.

What is claimed is:

1. An apparatus for extracting an obstruction located in a patient's vessel by fragmenting the obstruction and conveying fragments of the obstruction through the apparatus and out of the patient's body, comprising in combination:
    a flexible-tube, having an open distal end, and is connectable to a negative pressure,
    a motor-rotateable flexible conveyor-shaft that is disposed in the flexible tube
    at least a part of the flexible conveyor-shaft is a spiral wire with gaps between its coils to enable the spiral to convey fragments, the direction of the spiral is such that as it rotates relative to the flexible tube it conveys the fragments, cooperatively with the negative pressure, from the open distal end through the flexible tube,
    an offset agitator that at least partially extends out of the open distal end of the flexible-tube being connected to and rotated by the distal end of the flexible conveyor-shaft to fragment the obstruction while rotating with an effective diameter that is larger than its cross-sectional diameter,
    wherein the flexible conveyor-shaft and the offset agitator are a continuous spiral wire formed from flattened wire, the conveyor-shaft being made of the flattened wire wound on its edge and the offset agitator being made from the flattened wire wound on its side and wherein the conveyor-shaft and the offset agitator are connected one the other by a short section of twisted wire that is an integral part of the spiral wire that does not block fragments from entering the gaps between the coils of the conveyor shaft.

2. An apparatus for extracting an obstruction located in a patient's vessel by fragmenting the obstruction and conveying fragments of the obstruction through the apparatus and out of the patient's body, comprising in combination:
    a flexible-tube, having an open distal end, and is connectable to a negative pressure,
    a motor-rotateable flexible conveyor-shaft that is disposed in the flexible tube
    at least a part of the flexible conveyor-shaft is a spiral wire with gaps between its coils to enable the spiral to convey fragments, the direction of the spiral is such that as it rotates relative to the flexible tube it conveys the fragments, cooperatively with the negative pressure, from the open distal end through the flexible tube,
    an offset agitator that at least partially extends out of the open distal end of the flexible-tube being connected to and rotated by the distal end of the flexible conveyor-shaft to fragment the obstruction while rotating with an effective diameter that is larger than its cross-sectional diameter,
    the offset agitator is a spiral wire with gaps between its coils that are substantially smaller than the gaps between the coils of the flexible conveyor-shaft.

3. An apparatus for extracting an obstruction located in a patient's vessel by fragmenting the obstruction and conveying fragments of the obstruction through the apparatus and out of the patient's body, comprising in combination:
    a flexible-tube, having an open distal end, and is connectable to a negative pressure,
    a motor-rotateable flexible conveyor-shaft that is disposed in the flexible tube
    at least a part of the flexible conveyor-shaft being a spiral wire, the direction of spiral is such that as it rotates relative to the flexible tube it conveys the obstruction fragments, cooperatively with the negative pressure, from the open distal end through the flexible tube,
    a clearance between the flexible conveyor-shaft and the flexible tube being large enough so that the flexible conveyor-shaft rotates freely in the flexible tube and small enough so that the flexible conveyor-shaft radially supports the flexible tube to prevent it from kinking while the apparatus operates in a curved vessel,
    an offset agitator that at least partially extends out of the open distal end of the flexible-tube being connected to and rotated by the distal end of the flexible conveyor-shaft to fragment the obstruction while rotating with an effective diameter that is larger than its cross-sectional diameter.

4. An apparatus for extracting an obstruction located in a patient's vessel by fragmenting the obstruction and conveying fragments of the obstruction through the apparatus and out of the patient's body, comprising in combination:
    a flexible-tube, having an open distal end, and connectable to a negative pressure,
    a motor-rotateable flexible conveyor-shaft that is disposed in the flexible tube
    at least a part of the flexible conveyor-shaft is a spiral wire, the direction of spiral is such that as it rotates relative to the flexible tube it conveys the obstruction fragments, cooperatively with the negative pressure, from the open distal end through the flexible tube,
    an offset agitator that at least partially extends out of the open distal end of the flexible-tube being connected to and rotated by the distal end of the flexible conveyor-shaft to fragment the obstruction while rotating with an effective diameter that is larger than its cross-sectional diameter,
    wherein the offset-agitator can be moved in and out of the flexible tube, through the open distal end, to adjust the effective diameter of the offset agitator.

5. As in claim 1 wherein the cross-section of an outer diameter of the flexible conveyor-shaft is larger than the cross-section of an outer diameter of the offset agitator.

6. As in claim 1 wherein the flexible conveyor-shaft and the offset agitator are a continuous spiral wire and wherein the distal tip of the offset agitator is rounded.

7. As in claim 1 wherein the flexible conveyor-shaft and the offset agitator are a continuous spiral wire and wherein the distal tip of the offset agitator is an integral part of the wire that has been melted to form a rounded tip.

8. As in claim 1 wherein the flexible conveyor-shaft is made from a spiral wire with gaps between its coils to enable the spiral to engage with and convey the fragments and wherein an outer surface of the offset agitator is uninterrupted to reduce its likelihood of entanglement inside the vessel.

9. As in claim 1 wherein the flexible conveyor-shaft and the offset agitator are made from a spiral wire, the gap between the coils of the flexible conveyor-shaft are substantially larger than gap between the coils of the offset agitator.

10. As in claim 1 wherein a portion of the offset agitator that comes in contact with a wall of the vessel is smooth and another portion of the surface of the offset agitator is rough.

11. As in claim 1 wherein the flexible-tube transmits light across its wall.

12. As in claim 1 wherein the flexible-tube transmits light along its wall.

13. As in claim 1 wherein the apparatus is inserted into the vessel through an introducer having an inlet port that is connected to a pressurized fluid through a flexible line and the evacuation port that is connected to the negative pressure through a flexible line, wherein the flexible lines pass through valves that shut off the flow thought the lines when the motor is selectively disabled.

14. As in claim 1 wherein the flexible conveyor-shaft and the offset agitator are a continuous spiral wire that define a continuous passage that can accommodate a guidewire over which the flexible conveyor-shaft and the offset agitator can slide.

15. As in claim 2 wherein the cross-section of an outer diameter of the flexible conveyor-shaft is larger than the cross-section of an outer diameter of the offset agitator.

16. As in claim 2 wherein the flexible conveyor-shaft and the offset agitator are a continuous spiral wire and wherein the distal tip of the offset agitator is rounded.

17. As in claim 2 wherein the flexible conveyor-shaft and the offset agitator are a continuous spiral wire and wherein the distal tip of the offset agitator is an integral part of the wire that has been melted to form a rounded tip.

18. As in claim 2 wherein the flexible conveyor-shaft is made from a spiral wire with gaps between its coils to enable the spiral to engage with and convey the fragments and wherein an outer surface of the offset agitator is uninterrupted to reduce its likelihood of entanglement inside the vessel.

19. As in claim 2 wherein the flexible conveyor-shaft and the offset agitator are made from a spiral wire, the gap between the coils of the flexible conveyor-shaft are substantially larger than the gap between the coils of the offset agitator.

20. As in claim 2 wherein a portion of the offset agitator that comes in contact with a wall of the vessel is smooth and another portion of the surface of the offset agitator is rough.

21. As in claim 2 wherein the flexible-tube transmits light across its wall.

22. As in claim 2 wherein the flexible-tube transmits light along its wall.

23. As in claim 2 wherein the apparatus is inserted into the vessel through an introducer having an inlet port that is connected to a pressurized fluid through a flexible line and the evacuation port that is connected to the negative pressure through a flexible line, wherein the flexible lines pass through valves that shut off the flow thought the lines when the motor is selectively disabled.

24. As in claim 2 wherein the flexible conveyor-shaft and the offset agitator are a continuous spiral wire that define a continuous passage that can accommodate a guidewire over which the flexible conveyor-shaft and the offset agitator can slide.

25. As in claim 3 wherein the cross-section of an outer diameter of the flexible conveyor-shaft is larger than the cross-section of an outer diameter of the offset agitator.

26. As in claim 3 wherein the flexible conveyor-shaft and the offset agitator are a continuous spiral wire and wherein the distal tip of the offset agitator is rounded.

27. As in claim 3 wherein the flexible conveyor-shaft and the offset agitator are a continuous spiral wire and wherein the distal tip of the offset agitator is an integral part of the wire that has been melted to form a rounded tip.

28. As in claim 3 wherein the flexible conveyor-shaft is made from a spiral wire with gap between its coils to enable the spiral to engage with and convey the fragments and wherein an outer surface of the offset agitator is uninterrupted to reduce its likelihood of entanglement inside the vessel.

29. As in claim 3 wherein the flexible conveyor-shaft and the offset agitator are made from a spiral wire, the gap between the coils of the flexible conveyor-shaft are substantially larger than the gap between the coils of the offset agitator.

30. As in claim 3 wherein a portion of the offset agitator that comes in contact with a wall of the vessel is smooth and another portion of the surface of the offset agitator is rough.

31. As in claim 3 wherein the flexible-tube transmits light across its wall.

32. As in claim 3 wherein the flexible-tube transmits light along its wall.

33. As in claim 3 wherein the apparatus is inserted into the vessel through an introducer having an inlet port that is connected to a pressurized fluid through a flexible line and the evacuation port that is connected to the negative pressure through a flexible line, wherein the flexible lines pass through valves that shut off the flow thought the lines when the motor is selectively disabled.

34. As in claim 3 wherein the flexible conveyor-shaft and the offset agitator are a continuous spiral wire that define a continuous passage that can accommodate a guidewire over which the flexible conveyor-shaft and the offset agitator can slide.

35. As in claim 4 wherein the cross-section of an outer diameter of the flexible conveyor-shaft is larger than the cross-section of an outer diameter of the offset agitator.

36. As in claim 4 wherein the flexible conveyor-shaft and the offset agitator are a continuous spiral wire and wherein the distal tip of the offset agitator is rounded.

37. As in claim 4 wherein the flexible conveyor-shaft and the offset agitator are a continuous spiral wire and wherein the distal tip of the offset agitator is an integral part of the wire that has been melted to form a rounded tip.

38. As in claim 4 wherein the flexible conveyor-shaft is made from a spiral wire with gap between its coils to enable the spiral to engage with and convey the fragments and wherein an outer surface of the offset agitator is uninterrupted to reduce its likelihood of entanglement inside the vessel.

39. As in claim 4 wherein the flexible conveyor-shaft and the offset agitator are made from a spiral wire, the gap between the coils of the flexible conveyor-shaft are substantially larger than the gap between the coils of the offset agitator.

40. As in claim 4 wherein a portion of the offset agitator that comes in contact with a wall of the vessel is smooth and another portion of the surface of the offset agitator is rough.

41. As in claim 4 wherein the flexible-tube transmits light across its wall.

42. As in claim 4 wherein the flexible-tube transmits light along its wall.

43. As in claim 4 wherein the apparatus is inserted into the vessel through an introducer having an inlet port that is connected to a pressurized fluid through a flexible line and the evacuation port that is connected to the negative pressure through a flexible line, wherein the flexible lines pass through valves that shut off the flow thought the lines when the motor is selectively disabled.

44. As in claim 4 wherein the flexible conveyor-shaft and the offset agitator are a continuous spiral wire that define a continuous passage that can accommodate a guidewire over which the flexible conveyor-shaft and the offset agitator can slide.

* * * * *